United States Patent [19]

Guiset

[11] 4,183,102
[45] Jan. 15, 1980

[54] INFLATABLE PROSTHETIC DEVICE FOR LINING A BODY DUCT

[76] Inventor: Jacques Guiset, 62, rue Edouard Delesalle, Lille (Nord), France

[21] Appl. No.: 831,409

[22] Filed: Sep. 8, 1977

[51] Int. Cl.² .......................... A61F 1/00; A61F 1/24; A61M 29/02
[52] U.S. Cl. ................................................. 3/1.4; 3/1; 3/1.2; 128/334 R; 128/344; 128/348; 128/349 B; 128/351
[58] Field of Search ................. 3/1, 1.2, 1.4; 128/1 R, 128/129, 325, 334 R, 344, 348, 349 B, 349 BV, 350 R, 350 V, 351

[56] References Cited

U.S. PATENT DOCUMENTS

| | | | |
|---|---|---|---|
| 109,401 | 11/1870 | Faulkner | 128/129 |
| 2,548,602 | 4/1951 | Greenburg | 128/344 X |
| 2,883,986 | 4/1959 | De Luca et al. | 128/349 B |
| 3,154,077 | 10/1964 | Cannon | 128/349 B X |
| 3,435,824 | 4/1969 | Gamponia | 128/334 R |
| 3,509,884 | 5/1970 | Bell | 128/349 B |
| 3,516,408 | 6/1970 | Montanti | 128/334 R |
| 3,548,828 | 12/1970 | Vasile | 128/344 X |

OTHER PUBLICATIONS

"Intra-Arterial Instrumentation for Neurosurgery", by Alfred J. Lessenhop, The Bulletin of the Dow Corning Center for Aid to Medical Research, vol. 2, No. 3, Jul. 1960, p. 9.

Primary Examiner—Ronald L. Frinks
Attorney, Agent, or Firm—Robert E. Burns; Emmanuel J. Lobato; Bruce L. Adams

[57] ABSTRACT

The invention provides a prosthetic device for introduction into a duct and for lining an interior wall portion of the duct. The device comprises a generally toroidal, hollow, inflatable sleeve and means for introducing a pressurized fluid into the sleeve. The sleeve is made of a material that is impermeable to the pressurized fluid. At least the outer portion of the sleeve is made of a flexible material capable of deforming to conform to the shape of said interior wall portion of the duct. The device can be introduced into the duct and correctly positioned when it is in a deflated state. Subsequently, it is inflated by introducing the pressurized fluid. This causes the outer portion of the sleeve to expand and grip said interior wall portion of the duct, while leaving a central channel for the passage of the liquid in the duct. The device may also comprise a plurality of such sleeves connected together in a side-by-side relationship.

25 Claims, 9 Drawing Figures

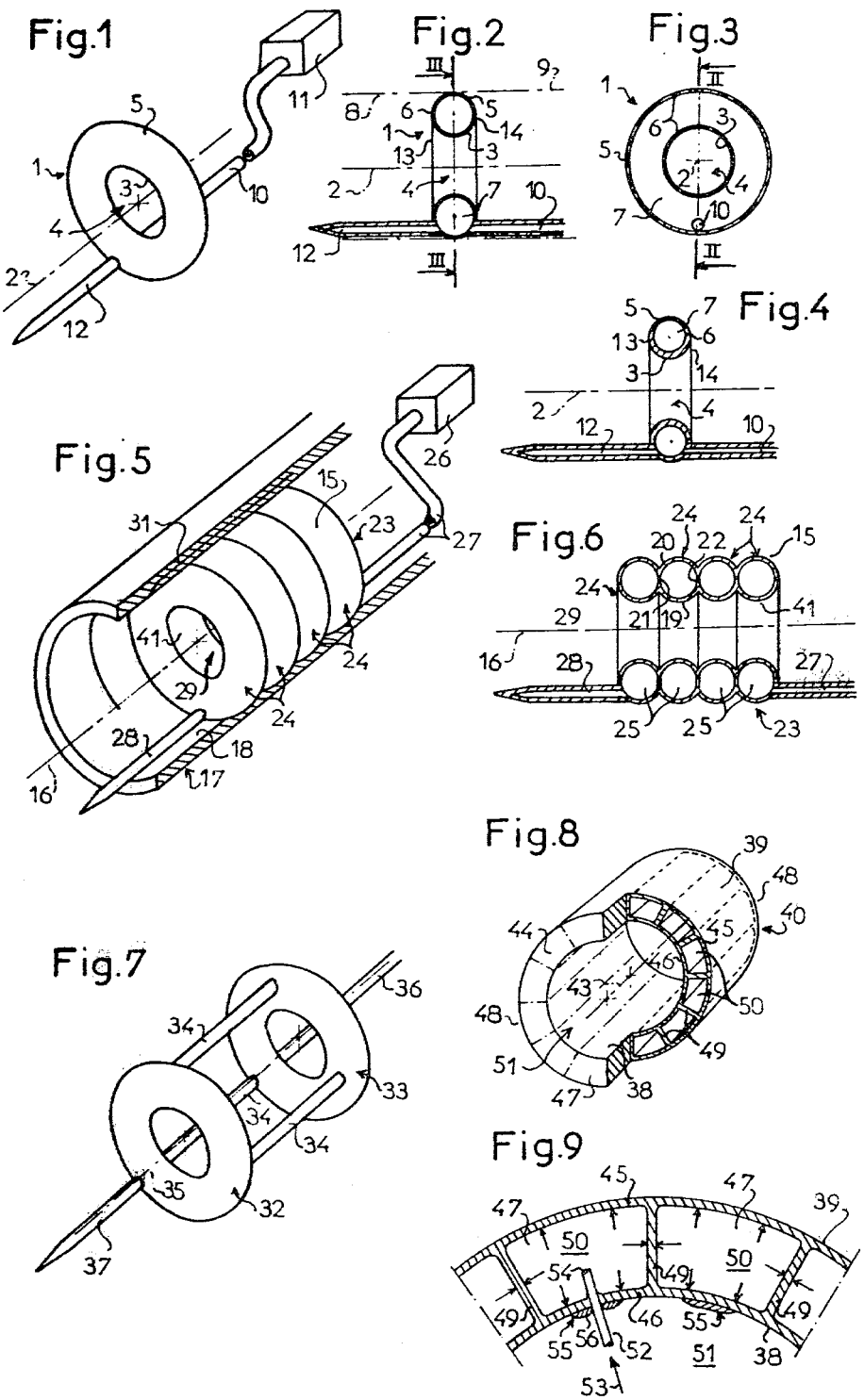

INFLATABLE PROSTHETIC DEVICE FOR LINING A BODY DUCT

BACKGROUND OF THE INVENTION

This invention relates to a prosthetic device and in particular to a prosthetic device intended to be introduced into the interior of a longitudinal duct and to be fixed to the wall of that duct, either temporarily or permanently, forming there a longitudinal channel.

The invention relates more particularly to the field of vascular surgery, but can also find applications in other fields and notably in tracheobranchial surgery. More generally, the invention finds use wherever it is essential to alleviate, either temporarily or permanently, an injury or defect to the wall of a passage while still permitting the circulation through the passage of the substances which should flow through it.

For example, in the vascular field, the aim of the invention is to provide a mechanical method which will enable the usually fatal afflication of aortal dissection to be treated, at least temporarily. It is known that this disease is characterised by the appearance in the aorta of a second flow parallel to the main flow, which penetrates into the wall of the aorta itself. At present, it responds solely to careful medical treatment, since any premature surgical intervention is fatal. Under medical treatment, however, it remains fatal in 90% of cases.

In this field, the aim of the invention is to provide a prosthetic device which, at least until surgical intervention becomes possible, enables the wall of the aorta to be joined up to interrupt the second flow and to prevent any extension of the dissection, while still of course permitting the normal flow to take place. Since such an effect cannot be produced by a device disposed outside the aorta, this prosthetic device must, of course, be capable of being introduced into the aorta, of being fixed in a position and in a form such that it pushes back the dissected wall outwards in such a manner as to bring the two parts thereof together to interrupt the second flow.

In other fields, the aim of the invention is to provide a prosthetic device which may be used to line a duct internally in a perforated or too permeable zone of the duct.

SUMMARY OF THE INVENTION

For this purpose, the prosthetic device according to the invention, intended to be introduced into the interior of a longitudinal duct and to be attached to the wall of that duct, forming there a longitudinal channel, is characterised in that it comprises at least one sleeve possessing an external face capable of fitting to the internal periphery of the duct, and an internal face intended to define within the sleeve said channel, passing through the sleeve from one end to the other, in that at least the external face of the sleeve is at least partially defined by a flexible, impermeable membrane, capable deforming at least outwards, opposite to which the sleeve possesses internally an impermeable chamber bounded at least partially by said membrane and capable of receiving internally a fluid under pressure, and in that means are provided for introducing into said chamber, when desired, a fluid under pressure, to permit the introduction of the sleeve into the duct with minimum bulk, and then to cause a deformation of the membrane towards the outside of the sleeve by inflation, and to cause the sleeve to be fixed by gripping of the membrane against the internal periphery of the duct.

BRIEF DESCRIPTION OF THE DRAWINGS

Several forms of prosthetic device, each constructed in accordance with the invention, will now be described, by way of example, with reference to the accompanying drawings, in which:

FIG. 1 is a perspective view of a first form of prosthetic device in accordance with the invention;

FIG. 2 is a cross-section of the device of FIG. 1 taken on the line II—II of FIG. 3;

FIG. 3 is a cross-section of the device of FIGS. 1 and 2 taken on the line III—III of FIG. 2;

FIG. 4 is a view similar to that of FIG. 2, but showing a modification of the prosthetic device of FIGS. 1 to 3;

FIG. 5 is a perspective view of another form of prosthetic device;

FIG. 6 is a longitudinal cross-section of the device of FIG. 5;

FIG. 7 is a perspective view of another form of prosthetic device;

FIG. 8 is a perspective view of another form of prosthetic device and shows a half-section through a transverse plane; and FIG. 9 shows a greatly enlarged detail of this transverse section.

DESCRIPTION OF PREFERRED EMBODIMENTS

Although the prosthetic devices described below can be partially formed of rigid material, these figures illustrated preferred cases, in which the prosthetic devices are entirely formed of flexible material. This permits the introduction and positioning of such a prosthetic device with a very reduced volume into the duct before inflating it in order to fix it at the desired position. These prosthetic devices have, therefore, been illustrated in the inflated state, that is to say in the form which they adopt when they are in use, since they are shapeless in the deflated state.

In the example illustrated in FIGS. 1 to 3, the prosthetic device is in the form of a hollow toroidal sleeve 1 whose axis 2 is intended to be placed along the axis of the duct to be lined. This sleeve 1 possesses, adjacent to the axis 2, a face 3 (the "internal face") defining, inside the sleeve, a channel 4 which passes through it from side to side along the axis 2. The sleeve 1 also possesses remote from the axis 2, a face 5 (the "exteral face") which is intended to contact the wall of the duct to be lined.

In this example, the sleeve 1 is defined by a single wall 6 which is closed onto itself so as to define between the faces 3 and 5 a toroidal chamber 7.

Although, as explained above, it could be formed partially of rigid material, the wall 6 of the sleeve 1 is in the form of a flexible, impermeable membrane which is deformable at least outwardly, that is to say in the direction of movement of the sleeve 1 away from its axis 2, at least at the external face 5. This outward deformation is accomplished, in the manner described below, by the introduction of a pressurized fluid into the interior of the chamber 7. Preferably, the membrane constituting the wall 6 is of an extensible material such as a compound of natural or synthetic rubber.

Now, if a pressurized fluid is introduced into the interior of the chamber 7, owing to the fact that the wall 6 offers to the interior of this chamber an area close to the external face 5 which is greater than the area which it offers at the internal face 3 (by reason of the larger diameter of the external face 5, as can be clearly seen in FIG. 3), the inflation of the sleeve 1 resulting therefrom leads essentially to a movement of its external face 5 away from the axis 2. This movement tends to cause a movement of the internal face 3 also in the direction away from the axis 2. This movement, being a function of the relative diameters of the internal and external faces 3 and 5 of the sleeve 1 and of the thickness of the wall 6 at these faces, may either limit the displacement towards the axis 2 which the internal face 3 tends to undergo during the inflation (as a result of the pressure which it receives from the interior of the chamber 7 towards the axis 2), or compensate or indeed over-compensate this tendency, by causing also a movement of the internal face 3 away from the axis 2 with an increase in the diameter of the channel 4.

In either of these cases, the expansion of the sleeve 1 maintains the existence of the channel 4, which remains open. The expansion of the sleeve 1 at the external face 5 permits the sleeve to be fixed against the internal periphery 8 of the duct 9 which is to be lined, by gripping against this internal periphery.

Various means, permanently fixed or not to the sleeve 1, may be provided for the purpose of introducing, when desired, the pressurized fluid into the chamber 7 for causing its inflation. In the case of the example illustrated in FIGS. 1 to 3, the sleeve 1 is permanently equipped with an impermeable, flexible tube 10, one end of which leads into the interior of the chamber 7 through the wall 6 with which it is integral. The other end of the tube is connected to a pressurized fluid source 11 of any known type, usually remaining outside the sleeved duct 91. The tube 10 penetrates into the duct 9 through the zone at which the sleeve 1 has been introduced.

In these circumstance, it is possible to introduce the sleeve 1 into the duct 9, with a minimum bulk, that is to say in practice totally deflated, through an orifice possessing sufficiently small dimensions to be without risk to the patient. The prosthetic device is then brought into the zone to be lined, for example by means of a probe, which may consist, for example, of an adaptation of the umbrella probe frequently used in surgery. Once it is in place, the prosthetic device is inflated by supplying into it pressurized fluid from the source 11. Depending upon the particular case, the device may either be left permanently in place, in which case it may be essential to reinflate it periodically to compensate for pressure losses which can result from a degrading with time of the material of which the wall 6 of the sleeve 1 is made, or it may be removed during a later surgical intervention, for example by deflating and then pulling on the tube 10. It may also be removed following upon the progressive deflation of the sleeve 1 referred to above.

In order to ensure correct positioning of the longitudinal axis 2 in coincidence with the axis of the duct 9 while the sleeve is being inflated, this sleeve is provided with a tube 12 of impermeable material, the tube being parallel to the axis 2, and close to the external face 5. A first end of the tube 12 leads into the interior of the chamber 7 through the wall 6, while the other end is closed. This tube 12 is fixed to the wall 6 in such a manner that, when the sleeve is inflated, it adopts a rectilinear form and is orientated parallel to the axis 2. Preferably, the connection between the tube 10 and the wall 6 of the sleeve is also formed in this manner and the two tubes 10 and 12 are situated one in the extension of the other. Thus, the inflation of the sleeve 1 which is accompanied by a stiffening of the tubes 10 and 12, causes these two tubes to bear against the internal periphery 8 of the duct and the axis 2 to become orientated parallel to this internal periphery 8, that is to say parallel to the axis of the duct 9.

According to a modification of this first form of prosthetic device, illustrated in FIG. 4, in which the same reference numerals have been used as were used in FIGS. 1 to 3, the wall 6 is stiffer at the internal face 3 of the sleeve 1 than at its external face 5. This greater rigidity in this region results from a greater thickness of the membrane at the internal face 3 with a progresive thinning towards the external face 5. This greater rigidity could, of course, be obtained by other means, notably by forming the wall of the sleeve 1 of a number of pieces of different natures, the pieces corresponding to the internal face 3 of the sleeve being the more rigid. The prosthetic device illustrated in FIG. 4 possesses, moreover, the same toroidal form about the axis 2 as the device illustrated in FIGS. 1 to 3.

If it is desired substantially to increase the dimension of the sleeve 1 in the longitudinal direction of its axis 2, particularly when the sleeve is integrally formed of a flexible material at least in the region of its internal face 3 and its external face 5, it is useful to create, between these two faces, bracings or diaphragms which transmit to the internal face the tendency of its external face to a movement outwards and away. In fact, it appears that if the distance between the elements of the sleeve 1 which join together the internal face 3 and the external face 5, and which consist, in the example illustrated in FIGS. 1 to 3, of two annular zones 13 and 14 orientated transversely with respect to the axis 2, is too large, the inflation of the sleeve tends to be accompanied by a shrinkage of the internal channel 4 at the half-way position between these elements.

FIGS. 5 and 6 illustrate a first type of such a braced prosthetic device 23. This device 23 possesses an internal face 41 and an external face 15, both being surfaces of revolution about a longitudinal axis 16 intended to coincide with the axis of the internal periphery 18 of a duct 17 to be lined. These faces 41 and 15 are defined respectively by the juxtaposition, in a longitudinal direction parallel to the axis 16, of the internal faces 19 and the external faces 20 of elementary toroidal sleeves 24 whose axes are coincident with the axis 16. Each of these sleeves 24 is analogous to the sleeve 1 illustrated in FIGS. 1 to 3 or to the sleeve of FIG. 4. The sleeves 24 are placed side-by-side and integrally connected by transverse annular zones such as 21 and 22, which are similar to the transverse zones 13 and 14 of the sleeve 1 illustrated in FIGS. 1 to 3, in order to define the device 23.

The sleeves 24 defining the device 23 may be identical to or different from one another. In the example illustrated there are four such sleeves 2 but it will be obvious that there could be either less than or more than this number depending upon the longitudinal dimension which it is desired to give to the prosthetic device 23 which itself is a function of the length of the zone of the duct 17 to be lined.

Each pair of adjacent internal chambers 25 (see FIG. 6) of the sleeves 24 are interconnected by at least one orifice passing through the appropriate bracing zones 21 and 22, in such a way as to ensure simultaneous inflation of all the sleeves.

This inflation is carried out from a pressurized fluid source 26 by means of a flexible tube 27 which is connected to one of the end sleeves 24 in a manner identical to the method of connecting the tube 10 to the sleeve 1 in the embodiment illustrated in FIGS. 1 to 3. The other end sleeve 24 carries a tube 28 analogous to the tube 12 of the embodiment of FIGS. 1 to 3, the tube 28 being connected to the wall of this sleeve in a manner identical to that in which the tube 12 is connected to the sleeve 1.

When the pressurized fluid is introduced into the communicating chambers 25 of the sleeves 24, each of these sleeves deforms at its internal face 19 and at its external face 20 in the same manner as the sleeve 1, and the inflation of the device 23 results in an outward displacement of its external force 15 accompanied by fixing against the internal periphery 18 of the duct 17. The internal face 41 maintains within the device 23 a longitudinal channel 29 defined by the mutual longitudinal prolongation of the different channels defined by the respective internal faces 19 of the sleeves 24 and of sufficient dimensions not to interfere with the circulation of the substances which normally circulate inside the duct 17.

The joined together zones 21 and 22 of the sleeves 24 behave, with respect to the internal face 41 and the external face 15 of the device 23, like bracing members interconnecting its faces 41 and 15 and transmitting to the latter the tendency of the former towards an outward movement during inflation.

This prosthetic device 23 has been illustrated in FIG. 5 in the inflated state, fixed inside the aorta 17 for the purpose of remedying, at least temporarily, an aortal dissection. It can be seen in this figure, that the external face 15 of the device 23 bears onto the dissected zone 31 to bring its two parts back into contact, at least in a longitudinally limited zone but over the entire cross-section of the aorta, by interrupting any passage of blood between these two parts to prevent the dissection from becoming extended. Naturally, such a prosthetic device 23 can be used for other purposes than the treatment of aortal dissections, and particularly for lining a duct, the wall of which is for example perforated. The imperviousness of the membranes constituting the walls of the sleeves 24 which is necessary for the purpose of inflating the device results in an imperviousness of this prosthetic device to the fluid or liquid which passes through the channel 29.

FIG. 7 shows another embodiment of prosthetic device which is formed from several sleeves analogous to the sleeve 1 illustrated in FIGS. 1 to 3 or the sleeve illustrated in FIG. 4. In this embodiment, two elementary sleeves 32 and 33 (which in the present case are identical but could be different from one another) are connected together by three bracing members 34 holding them when inflated in a position such that their respective longitudinal axes define a common longitudinal axis 35. Obviously, the number of sleeves and the number of bracing members could be varied.

The bracing members 34 keep the two sleeves 32 and 33 apart, and are preferably constituted of tubes of flexible impermeable material which are oriented parallel to the longitudinal axis 35. Each of the bracing members 34 communicates at both of its ends respectively with the internal chamber of the sleeve 32 and with the internal chamber of the sleeve 33.

The sleeve 33 carries a flexible tube 36, connected to a pressurized fluid source (not shown) for the introduction of pressurized fluid into the two sleeves 32 and 33 and into the tubular bracing members 34 in order to give to them the illustrated shape and to inflate the two sleeves, for the purpose of fixing them against the internal periphery of the duct to be lined. The sleeve 32 carries a tube 37 analogous to the tube 12 of the embodiment illustrated in FIGS. 1 to 3. The tubes 36 and 37 are preferably connected respectively to the sleeve 33 and the sleeve 32 in the same manner as the tubes 10 and 12 are connected to the sleeve 1 in the embodiment illustrated in FIGS. 1 to 3, in order that each of them shall adopt an orientation parallel to the axis 35 when the pressurized fluid is introduced into the interior of the prosthetic device.

FIGS. 8 and 9 illustrate a form of prosthetic device in which the bracing members interconnecting the internal face 38 and the external face 39 of a sleeve 40 consist essentially of partitions oriented longitudinally instead of being oriented transversely as in the embodiment illustrated in FIGS. 5 and 6. In this case, the internal face 38 and the external face 39 are cylinders having a common longitudinal axis 43. The two faces 38 and 39 are together at the transverse ends of the sleeve 40 by two transverse annular faces such as 44. Other forms could, of course, also be envisaged without thereby departing from the scope of this invention, and particularly elliptical shapes, truncated conical shapes of revolution or not of revolution, etc. would be possible.

The external face 39 and the internal face 38 of the sleeve 40 are defined by impervious flexible membranes 45 and 46, which are extensible at least in a circumferential direction. Preferably, these membranes 45 and 46 are elastically extensible and are formed, for example, of natural or synthetic rubber. It is not essential for the faces 38 and 39 to be completely flexible, but they must be at least partially flexible.

The space between the two membranes 45 and 46 is partitioned by transverse membranes 47, which are extensible at least in a circumferential direction, and by twelve longitudinal membranes 49 which are, for example, oriented radially. The transverse membranes 47 are preferably elastically extensible and the longitudinal membranes 49 are preferably extensible only slightly. For reasons of convenience in manufacture, both sets of membranes 47 and 49 are, however, generally flexible.

The sleeve 40 illustrated comprises only two transverse membranes 47, each of which is impermeable and interconnects the membranes 45 and 46 in the immediate proximity of one transverse end 48 of the sleeve and defines the annular face 44 at that end. Depending upon the longitudinal dimensions of the sleeve 40 or in order to satisfy special requirements such as the progressiveness of inflation in a longitudinal direction, it would, of course, also be possible to provide intermediate and similar transverse partitions.

The longitudinal membranes 49 are positioned between the membranes 45 and 46 and the membranes 47. They may be impermeable and contiguous in an impermeable manner with the membranes 45, 46 and 47 in order to define with them sealed chambers 50, here oriented longitudinally. These chambers 50 could also communicate with one another through the membranes 49.

Means are also provided for introducing a gas, when desired, into the different chambers 50, either simultaneously or successively, in order to cause the chambers to inflate. As a result of the inflation and the consequent increase in the circumferential dimensions of the membranes 45 to 47, a simultaneous increase in the external diameter of the external face 39 and in the internal diameter of the internal face 38, which defines the channel 51, results. This means may, of course, be of any suitable type and in particular may be identical to that with which the previously described sleeves are equipped. In FIG. 9, however, a different form of inflation means is shown, which may also be used for all the inflatable prosthetic devices described above.

According to this preferred embodiment, the sleeve 40 is equipped so that each of its chambers 50 can be inflated by means of a hollow needle 52 which is connected to a pressurized fluid source indicated diagrammatically by an arrow 53. The end 54 of the needle 52 is introduced into each of the chambers 50, in turn, by piercing one of the membranes bounding that chamber, for example the internal membrane 46. In order that this piercing by means of the needle 52 shall not cause the membrane such as 46 to tear, and in order that this membrane shall close again after the needle has been extracted, this membrane is provided in the region of each of the chambers 50 with at least one reinforced zone. In the example illustrated, this reinforced zone 55 is defined by a disc 56 connected over its entire area with the membrane 46, for example by gluing to that membrane. The disc 56 is elastically extensible, but preferably possesses a lower extensibility than that of the membrane 46, so as to facilitate closing of the latter after the needle 52 has been extracted.

It should be noted that such an arrangement can be adopted, not only for elastically extensible membranes, but also for non-elastic membranes, which may then be equipped with an orifice obturated by a disc such as 56, for the purpose of introducing the needle 52.

Such a method of inflation by means of a needle has the advantage of not requiring any valve (other than that provided by the natural elasticity of the disc 56), and of not necessitating any connecting or disconnecting operation, such operations usually being difficult to carry out while the prosthetic device is in place. Moreover, this method does not require the permanent presence of a connecting tube leading to the pressurized fluid source, as was the case in the other embodiments described.

This prosthetic device illustrated in FIGS. 8 and 9 can be varied in a number of ways. In particular, it may comprise a variable number of transverse membranes and of internal longitudinal membranes, the numbers of which will depend upon its dimensions and any particularly desired inflation effects. These membranes may then be arranged uniformly or non-uniformly distributed in the sleeve.

Different methods of manufacture of this prosthetic device can also be envisaged. In the simple embodiment illustrated, which corresponds to the most frequent case, the external membrane 45, the internal membrane 46 and the longitudinal membranes 49 may be formed in one piece by extrusion, after which the transverse membranes 47 are joined on. Alternatively, each chamber 50 may be bounded externally by a tube of impermeable, flexible and generally elastically extensible material, the wall of which defines both the external membrane 45 and the internal membrane 46 of this chamber, and also the longitudinal membranes 49 and transverse membranes 47 defining this chamber with the external and internal membranes. The sleeve is then formed by juxtaposing the desired number of tubes, which are then connected together in generally longitudinal zones corresponding to the membranes 49. It should be noted that in this case, as in the preceding one, non-deformable zones, particularly longitudinal zones but optionally also transverse zones, may be incorporated between the different extensible chambers. It should, however, be noted that, in order to obtain a simultaneous expansion of the internal and external diameters of the sleeve, the area of the external membrane related to each chamber or group of chambers is preferably greater than the area of the internal membrane related to these same chambers. Where applicable, it is also possible to modify the elasticity and extensibility of the different membranes by varying their thickness and/or the material of which they are made.

Other forms of prosthetic device could also be envisaged, particularly as combinations of the different embodiments described. It would be possible, in particular, to envisage an embodiment having bracing members interconnecting the two faces of the sleeve which is intermediate between the forms illustrated respectively in FIGS. 5 and 6 and in FIGS. 8 and 9, in which the bracing members would possess the form of partitions of helical shape about the axis of the prosthetic device. Bracing members in the form of ties and not of partitions could also be used.

Finally, although it would be preferable for the prosthetic devices to be integrally formed of flexible material, it is also possible for them to be made partially of rigid or semi-rigid material. This is particularly the case in regard to the longitudinal bracing members of FIGS. 8 and 9 or to bracing members in the form of ties, in regard to the internal face of the sleeve and in regard to the tube such as 12, 28 or 37 ensuring the orientation of the prosthetic device in the duct. This tube may, for example, act as a removable extension of a probe used for placing the device in position.

I claim:

1. A prosthetic device for introduction into a duct and for lining an interior wall portion of the duct, the device comprising a plurality of interconnected generally toroidal, hollow, inflatable sleeves and means for introducing a pressurized fluid into the sleeves, said sleeves being made of a material that is impermeable to the pressurized fluid, wherein at least the outer portions of the sleeves are made of a flexible material capable of deforming to conform to the shape of said interior wall portion of the duct, whereby the device can be introduced into, and positioned within, the duct in a deflated stated and then inflated by introducing the pressurized fluid so that the said outer sleeve portions grip said interior wall portion of the duct and so that a longitudinal channel is defined along the axis of the generally toroidal sleeves, and means for assuring orientation of said sleeves in said duct such that the longitudinal direction of said channel coincides with the longitudinal direction of the duct at least after inflation of the device, said means for assuring orientation comprising at least one tube of impermeable material connected at one end with an end sleeve and closed at the other end, said tube extending in the longitudinal direction of said channel when pressurized fluid is introduced into the interiors of said sleeves.

2. A prosthetic device according to claim 1, wherein adjacent sleeves are connected together by means of bracing elements.

3. A prosthetic device according to claim 2, wherein each bracing element is a hollow, tubular member made of flexible, impermeable material whose interior is in fluid communcation with the interior of each of the sleeves connected thereby.

4. A prosthetic device for introduction into a duct and for lining an interior wall portion of the duct, said device comprising a generally toroidal, hollow, inflatable sleeve having an internal wall defining an internal longitudinal channel, and an external wall which is defined at least partially by a flexible, impermeable membrane capable of deforming at least outwardly and which is capable of adapting itself to the shape of said interior wall portion of the duct, means for introducing a pressurized fluid into the sleeve interior, the walls of the sleeve being impermeable to the pressurized fluid, whereby the device can be introduced into, and positioned within, the duct in a deflated state and then inflated by introducing pressurized fluid into said sleeve so that the external wall grips said interior wall portion of the duct and so that the channel remains open, and means for assuring orientation of said sleeve in said duct such that the longitudinal direction of the channel bounded by said internal wall coincides with the longitudinal direction of the duct at least after inflation of the device, to fix it in the duct, said means for assuring orientation of the sleeve comprising at least one tube of impermeable material integral with said sleeve, connected with said sleeve at one of its ends and closed at the other end, said tube extending in the longitudinal direction of said channel when pressurized fluid is introduced into the interior of said sleeve.

5. A prosthetic device according to claim 4, wherein said internal wall of the sleeve comprises a flexible, impermeable, deformable membrane.

6. A prosthetic device according to claim 5, wherein the membrane of the external wall of said sleeve is more deformable than the membrane of the internal wall.

7. A prosthetic device according to claim 5, wherein said sleeve is formed of a flexible, impermeable membrane, closed onto itself to define said sleeve.

8. A prosthetic device according to claim 5, wherein bracing members are provided joining together the membrane of the internal wall of said sleeve and the membrane of the external wall.

9. A prosthetic device according to claim 8, wherein said membranes and said bracing members are made of the same material.

10. A prosthetic device according to claim 8, wherein said bracing members consist of substantially transverse partitions between said membranes.

11. A prosthetic device according to claim 7, wherein said sleeve consists of at least one hollow torus of flexible, impermeable material.

12. A prosthetic device according to claim 5, wherein said means for introducing a pressurized fluid comprises at least one tube of impermeable flexible material integral with said sleeve which leads into the interior of said sleeve and is connected to a pressurized fluid source.

13. A prosthetic device according to claim 4, wherein said means for introducing a pressurized fluid comprises at least one elastically extensible and reinforced zone of the impermeable wall of the sleeve, said zone being capable fo being perforated by a hollow needle connected to a pressurized fluid source and of reclosing elastically after the needle has been withdrawn.

14. A prosthetic device according to claim 12, wherein said tube assuring orientation of said sleeve and said tube for introducing pressurized fluid are situated the one in a prolongation of the other.

15. A prosthetic device according to claim 4, wherein said tube assuring the orientation of the sleeve is integral with the sleeve in the immediate proximity to the external wall of said sleeve.

16. A prosthetic device according to claim 5 wherein said membranes are made of an extensible material.

17. A prosthetic device for introduction into a duct and for lining an interior wall portion of the duct, the device comprising a plurality of generally toroidal, hollow, inflatable sleeves placed side-by-side with side walls of adjacent sleeves integrally joined with one another, inner walls of said sleeves being juxtaposed to define an internal longitudinal channel, outer walls of said sleeves being adapted to engage the interior wall of said duct and said integrally joined side walls forming transverse partitions connecting said inner and outer walls, said sleeves being made of a material that is impermeable to the pressurized fluid, wherein at least the outer wall of each sleeve is made of flexible material capable of deforming to conform to the shape of said interior wall portion of the duct, and means for introducing a pressurized fluid into said sleeves, said side walls being apertured to connect the interiors of said sleeves with one another to supply pressurized fluid to all of said sleeves, whereby the device can be introduced into, and positioned within, said duct in a deflated state and then inflated by introducing the pressurized fluid into said sleeves so that said outer walls of said sleeves grip said interior wall portion of the duct and so that a longitudinal channel is defined by the inner walls of the sleeves.

18. A prosthetic device according to claim 17, wherein said sleeves are all identical toruses.

19. A prosthetic device according to claim 17, wherein said inner walls of said sleeves are less flexible than said outer walls.

20. A prosthetic device according to claim 17, wherein said means for introducing pressurized fluid into said sleeves comprises a flexible tube connected to one of the end sleeves of said device.

21. A prosthetic device according to claim 20, further comprising means for assuring orientation of said sleeves in said duct such that the longitudinal direction of said channel defined by inner walls of said sleeves coincides with the longitudinal direction of the duct at least after inflation of the devices, said means for assuring orientation comprising a tube extending from the other end sleeve of said device and closed at its outer end.

22. A prosthetic device according to claim 21, wherein said tube for assuring orientation of said sleeves is at least approximately aligned with said tube for introducing pressurized fluid into said sleeves.

23. A prosthetic device according to claim 22, wherein said tubes are connected with said end sleeves respectively near the outer walls of said sleeves.

24. A prosthetic device according to claim 21, wherein said tube for assuring orientation of said sleeves is flexible and inflatable and is in communication with the interior of said sleeves, whereby it is inflated when pressurized fluid is introduced into said sleeves.

25. A prosthetic device according to claim 17, wherein there are at least four of said toroidal sleeves joined side-by-side.

* * * * *